United States Patent [19]
De Flora et al.

[11] Patent Number: 6,040,297
[45] Date of Patent: Mar. 21, 2000

[54] DINUCLEOSIDE-5',5'-PYROPHOSPHATES

[75] Inventors: Antonio De Flora; Umberto Benatti, both of Genoa; Marco Giovine, Finale Ligure, all of Italy

[73] Assignees: Biosearch Italia, S.p.A.; Gruppo Lepetit, S.p.A., both of Italy

[21] Appl. No.: 08/776,138

[22] PCT Filed: Jul. 10, 1995

[86] PCT No.: PCT/EP95/02676

§ 371 Date: Jan. 14, 1997

§ 102(e) Date: Jan. 14, 1997

[87] PCT Pub. No.: WO96/02554

PCT Pub. Date: Feb. 1, 1996

[30] Foreign Application Priority Data

Jul. 15, 1994 [EP] European Pat. Off. .............. 94202059

[51] Int. Cl.[7] .......................... A61K 31/70; C07H 19/207
[52] U.S. Cl. ................ 514/47; 514/48; 514/51; 536/26.23
[58] Field of Search ................ 514/47, 48, 51; 536/26.23

[56] References Cited

U.S. PATENT DOCUMENTS

| | | | |
|---|---|---|---|
| 3,321,463 | 5/1967 | Moffatt | 536/26.23 |
| 3,506,478 | 4/1970 | Myers | 536/26.23 |
| 4,855,304 | 8/1989 | Devash | 514/47 |
| 5,159,067 | 10/1992 | Schinazi et al. | 536/26.23 |
| 5,521,161 | 5/1996 | Malley et al. | 514/45 |

FOREIGN PATENT DOCUMENTS

| | | |
|---|---|---|
| 0192315 | 8/1986 | European Pat. Off. . |
| 0284405 | 9/1988 | European Pat. Off. . |
| 0298280 | 1/1989 | European Pat. Off. . |
| 0375183 | 6/1990 | European Pat. Off. . |
| 0392791 | 10/1990 | European Pat. Off. . |
| 9222306 | 12/1992 | WIPO . |

OTHER PUBLICATIONS

Tonetti et al., "Liver Targetting of Autologous Erythrocytes Loaded with Doxorubicin," *European J. Cancer*, 27(7), 947–948 (Jul. 1991).

DeFlora et al., "Engineered Erythorcytes as Carriers and Bioreactors," in *Generation of Antibodies by Cell and Cell Immortalization, The Year in Immunology*, vol. 7, Terhorst et al, (eds.). Karger, New York, NY, 1993, pp. 168–174.

Hagemeier et al., "High–Performance Liquid Chromatographic Methods for Separation of Dinucleotides," *J. Chromatography*, 237(1), 174–177 (Mar. 5, 1982).

Iwase et al., "Molecular Design of a Eukaryotic Messenger RNA and Its Chemical Synthesis," *Nucleic Acids Res.*, 20(7), 1643–1648 (Apr. 11, 1992).

Bornemann et al., "Darstellung 5',5"–Phosphatverknüpfter Dinucleoside," *Z. Naturforschung*, 36c(1/2), 135–141 (Jan./Feb., 1981).

Magnani et al., "Synthesis and Targeted Delivery of an Azidothymidine Homodinucleotide Conferring Protection to Macrophages Against Retroviral Infection," *Proc. Nat. Acad. Sci. USA*, 93(9), 4403–4408 (Apr. 30, 1996).

Benatti et al., "Azidothymidine Homodinucleotide–Loaded Erythrocytes as Bioreactors for Slow Delivery of the Antiretroviral Drug Azidothymidine," *Biomedical Biophysical Res. Comm.*, 220(1), 20–25 (Mar. 7, 1996).

Michelson et al., "Synthesis of Nucleoside Anhydrides by Anion Exchange," *Biochem. Biophys. Acta*, 91(1), 1–13 (Sep. 11, 1964).

Puech et al., Antiviral Res., 12:11–23 (1990), Synthesis and biological evaluation of dinucleoside methylphosphonates of 3'–azido–3'deoxythymidine and 2',3'–dideoxycytidine (Month of publication data unavailable).

Schinazi et al., Antimicrobial Agents and Chemotherapy, 34(6):1061–1067 (1990), (Jun., 1990) "Activities of 3'–Azido–3'–Deoxythymidine Nucleotide Dimers in Primary Lymphocytes Infected with Human Immunodeficiency Virus Type 1".

*Primary Examiner*—John Kight
*Assistant Examiner*—L. Eric Crane
*Attorney, Agent, or Firm*—Killworth, Gottman, Hagan, & Schaeff L.L.P.

[57] ABSTRACT

5,5'-Pyrophosphates of non-naturally occurring nucleosides selected from 1-(1-thyminyl)-3-azido-2, 3-dideoxy-D-riboside, 1(5-fluoro-1-uracilyl)-2, 3-dideoxy-D-riboside, 1-(1-uracilyl)-3-azido-2, 3-dideoxy-D-riboside, 1-(9-guaninyl)-2, 3-dideoxy-D-riboside, 1-(9-hypoxanthinyl)-2, 3-dideoxy-D-riboside, 1-(1-cytosinyl)-2, 3-dideoxy-D-riboside, and 1-(9-adeninyl)-2, 3-dideoxy-D-riboside, are described as well as their manufacture and use as therapeutic agents against tumors and retroviral infections including HIV infections. The compounds may be administered as the active ingredients of pharmaceutical compositions or as prodrugs encapsulated within biological carriers, e.g. transformed erythrocytes, for targeting to specific cell populations responsible for the development of the noted pathological disorders.

16 Claims, 3 Drawing Sheets

DINUCLEOSIDE-5',5'-PYROPHOSPHATES

This invention relates to dinucleoside-5',5'-$P^1,P^2$-pyrophosphates of the formula (I):

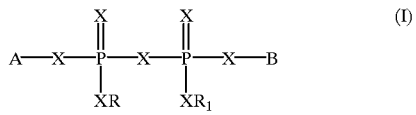

wherein:
the symbols A and B each independently represent a 5'-C' radical of a non-naturally occurring nucleoside selected from thymine-3'-azido-2',3'-dideoxy-D-riboside, 5-fluorouracil-2'-deoxy-D-riboside, uracil-3'-azido-2', 3'-dideoxy-D-riboside, guanine-2',3'-dideoxy-D-riboside, hypoxanthine-2',3'-dideoxy-D-riboside, cytosine-2',3'-dideoxy-D-riboside, and adenine-2',3'-dideoxy-D-riboside;

the symbols X each independently represent oxygen or sulfur;

the symbols R and $R_1$ each independently represent hydrogen or an alkyl group of from 1 to 10 carbon atoms;

and the addition salts of the compounds of formula (I) wherein R and/or $R_1$ represent hydrogen with bases providing biologically acceptable cations.

This invention includes also a process for the preparation of the dinucleoside-5',5'-$P^1,P^2$-pyrophosphates of formula (I), a method for their encapsulation into biological carriers, in particular erythrocytes, for targeting the above compounds to specific sites or cell populations which are involved in the development or responsible of pathological disorders such as tumors or viral infections, and compositions containing said biological carriers, in particular erythrocytes, encapsulating the dinucleoside-5',5'-$P^1,P^2$-pyrophosphates of formula (I).

Chemical modification of the erythrocytic membrane to encapsulate biologically active molecules is a powerful method to deliver to target cells the encapsulated molecule in a biologically active form. See, for instance;

De Flora A. et al. "Engineered erythrocytes as carriers and bioreactors". The Year in Immunology, Basel, Karger, (1993), Vol. 7, 168–174.

Tonetti M. et al. "Liver targeting of autologous erythrocytes loaded with doxorubicin". Eur. J. Cancer, (1991), Vol. 27, No. 7, 947–948.

Zocchi E. et al. "Human and murine erythrocytes as bioreactors releasing the antineoplastic drug 5-fluoro-2'-deoxyuridine". Advances in Biosciences, (1991), Vol. 81, Pergamon Press plc. 51–57.

De Flora A. et al. "Conversion of encapsulated 5-fluoro-2'-deoxyuridine-5'-monophosphate to the antineoplastic drug 5-fluoro-2'-deoxyuridine in human erythrocytes". Proc. Natl. Acad. Sci. USA, (1988), Vol. 85, 3145–3149.

De Flora A. et al. "The technology of carrier erythrocytes: a versatile tool for diagnosis and therapy". Biotechnology in Diagnostics, Elsevier Science Publishers B.V., (1985), 223–236.

Further literature in the field is cited in the above mentioned articles and publications.

In the following description and claims the correspondence between chemical names and commonly used acronyms will be maintained, as reported below:

thymine-3'-azido-2',3'-dideoxy-D-riboside (AZT), adenine-2',3'-dideoxy-D-riboside (DDA), 5-fluorouracil-2'-deoxy-D-riboside (FDU), cytosine-2', 3'-dideoxy-D-riboside (DDC), uracil-3'-azido-2',3'-dideoxy-D-riboside (AZDDU), hypoxanthine-2',3'-dideoxy-D-riboside (DDI), and guanine-2',3'-dideoxy-D-riboside (DDG).

Methods of encapsulating biologically active substances, in particular, phosphorylated compounds, into transformed erythrocytes and compositions for their use, as well as methods for inducing animal derived cells, especially erythrocytes to selectively seek out and fuse with other cells, have been disclosed also in patent literature: International Patent Application Publication No. 92/22306, U.S. Pat. No. 4,931,276, U.S. Pat. No. 4,652,449 and European Patent Application Publication No. 298280.

International Patent Application Publication No. WO 91/00867 describes 5'-diphosphohexose nucleosides having biological activity including antiviral activity.

In this description and claims, the expression "5'-C' radical of a non-naturally occurring nucleoside" identifies a radical derived from a non-naturally occurring nucleoside by removal of the hydroxy group in position 5' of the pentose moiety.

The expression "the symbols X each independently represent oxygen or sulfur" means that each of the symbols X may represent an oxygen or sulfur atom independently of the meanings assumed by the others. According to a preferred embodiment of this invention, either all symbols X represent oxygen or only one or two of them represent(s) sulfur and the others represent oxygen. In this latter case, the most preferred compounds of formula (I) are those wherein the symbol(s) X representing sulfur is(are) that(those) directly linked to the phosphorus atom(s) through a double bond or that(those) which is(are) part of the moiety XR or(and) $XR_1$.

The term "a biologically acceptable cation" means a cation which is suitable for the use in the pharmaceutical pratice and includes those cations which are not toxic for the biological carriers of the compounds of formula (I) and are compatible with the procedures for their encapsulation into said carriers. When the symbol R and/or $R_1$ independently represent(s) hydrogen, the compounds of formula (I) may form addition salts with bases providing biologically acceptable cations. Such salts may be represented by compounds of formula (I) wherein the symbol X of the moiety XR and/or $XR_1$ represent(s) an oxygen and/or sulfur atom in the anion form (i.e. $O^-$ and/or $S^-$) and the symbol R and/or $R_1$ represent(s) a biologically acceptable cation.

Cations which are acceptable for use in the pharmaceutical practice, are those deriving from the alkali or alkaline-earth metals, such as, sodium, potassium and magnesium, ammonia, and aliphatic, alicyclic and aromatic amines, such as, methylamine, dimethylamine, triethanolamine, piperidine, piperazine, n-methylpiperidine, n-methylpiperazine, morpholine and picoline.

Biologically acceptable cations suitable for both the use in the pharmaceutical practice and the encapsulation procedures are, for instance, $Na^+$ and $K^+$.

The term "an alkyl group of from 1 to 10 carbon atoms" identifies a linear or branched alkyl radical which may optionally contain an unsaturation and/or one or two substituents selected from hydroxy, mercapto, chloro, iodo, fluoro, bromo, amino, $(C_1-C_4)$alkylamino, di-$(C_1-C_4)$alkylamino, $(C_1-C_4)$alkoxy and $(C_1-C_4)$alkylthio. Preferably, the above term identifies an alkyl radical of 1 to 4 carbon atoms such as methyl, ethyl, propyl, 1-methylethyl, butyl, 1-methylpropyl, 1,1-dimethylethyl, and 2-methylpropyl which may optionally contain one or two substituents as defined above.

A further preferred group of compounds of this invention, includes those compounds of formula (I) wherein the symbols A, B and X are as specified above and the symbols R and $R_1$ each independently represent hydrogen, or a ($C_1$–$C_4$) alkyl as defined above. This group of preferred compounds includes also the addition salts of the compounds of formula (I) wherein R and/or $R_1$ represent(s) hydrogen with bases providing biologically acceptable cations such as $Na^+$, $K^+$, and the other cations mentioned above.

A most preferred group of compounds of this invention is individuated by those derivatives of formula (I) wherein the symbols A and B are as specified above, all symbols X represent oxygen and both R and $R_1$ represent hydrogen, and their salts with biologically acceptable cations, for example $Na^+$ or $K^+$.

Some specific examples of dinucleoside-5',5'-$P^1$,$P^2$-pyrophosphates of formula (I) which may illustrate this invention are specifically represented in the following Table I.

TABLE I

| A | B |
|---|---|

TABLE I-continued

| | A | B |
|---|---|---|
| 4) | 5-fluorouracil nucleoside (3'-OH, 5'-CH2–) | cytosine nucleoside (5'-CH2–, 3'-H) |
| 5) | 5-fluorouracil nucleoside (3'-OH, 5'-CH2–) | thymine nucleoside (5'-CH2–, 3'-N3) |
| 6) | 5-fluorouracil nucleoside (3'-OH, 5'-CH2–) | hypoxanthine nucleoside (5'-CH2–, 3'-H) |
| 7) | thymine nucleoside (3'-N3, 5'-CH2–) | hypoxanthine nucleoside (5'-CH2–, 3'-H) |
| 8) | thymine nucleoside (3'-N3, 5'-CH2–) | cytosine nucleoside (5'-CH2–, 3'-H) |

TABLE I-continued

| | A | B |
|---|---|---|
| 9) | thymine-deoxyribose with N₃ at 3' position | adenine-deoxyribose |
| 10) | adenine-deoxyribose | adenine-deoxyribose |
| 11) | hypoxanthine-deoxyribose | adenine-deoxyribose |
| 12) | hypoxanthine-deoxyribose | hypoxanthine-deoxyribose |
| 13) | hypoxanthine-deoxyribose | cytosine-deoxyribose |

TABLE I-continued

| | A | B |
|---|---|---|
| 14) | | |
| 15) | | |
| 16) | | |
| 17) | | |
| 18) | | |

TABLE I-continued

| A | B |
|---|---|
| 19) 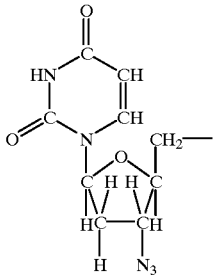 | 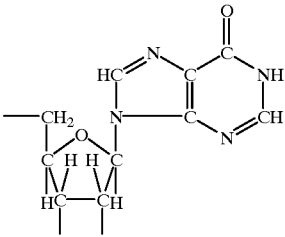 |
| 20) 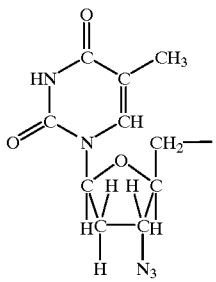 | 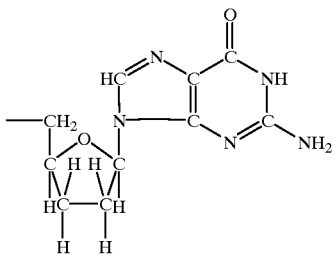 |
| 21) 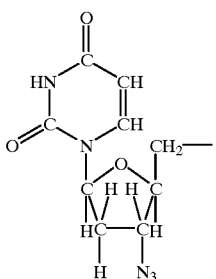 | 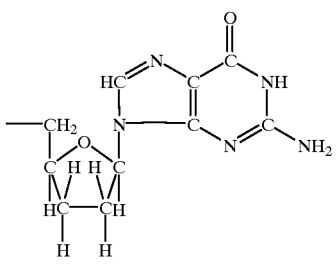 |

The dinucleoside-5',5'-$P^1$,$P^2$-pyrophosphates of formula (I) above wherein at least one of A and B represents a 5'-C' radical deriving from 5-fluorouracil-2'-deoxy-D-riboside are useful as antitumor therapeutical agents while the dinucleoside-5',5'-$P^1$,$P^2$-pyrophosphates wherein at least one of A and B represents a 5'-C' radical of a non-naturally occurring nucleoside selected from thymine-3'-azido-2',3'-dideoxy-D-riboside, uracil-3'-azido-2',3'-dideoxy-D-riboside, guanine-2',3'-dideoxy-D-riboside, hypoxanthine-2',3'-dideoxy-D-riboside, cytosine-2',3'-dideoxy-D-riboside, and adenine-2',3'-dideoxy-D-riboside, are useful as antiviral therapeutical agents, in particular, against retroviral infections, such as HIV infections.

According to the above described properties, the dinucleosides which contain both types of 5'-C' radicals as defined above, may be useful both as antitumor and antiviral agents.

The process for preparing the dinucleoside-5',5'-$P^1$,$P^2$-pyrophosphates runs according to procedures already described in the art. See for example: A. M. Michelson, "Synthesis of nucleotide anhydrides by anion exchange", in Biochim. Biophys. Acta, (1964), 91, 1–13. According to this procedure, a nucleoside phosphate of the formula (II):

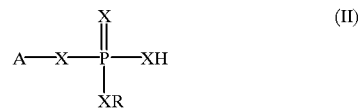

(II)

wherein A, X and R have the same meanings as above, is activated on the XH group of the phosphoric acid moiety by reaction with an activating agent, such as tetraphenyl pyrophosphate or diphenyl phosphochloridate, to form an activated phospho-ester of the above nucleoside phosphate. The activated phospho-ester is then reacted with a nucleoside phosphate of the formula (III):

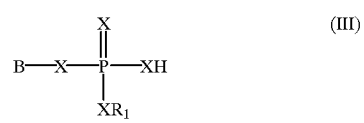

(III)

wherein B, X and $R_1$ have the same meanings as above, to form the compound of formula (I) by displacement of the activated diphenyl phosphate moiety from the activated phospho-ester.

Other examples of methods useful for preparing the dinucleoside-5',5'-P¹,P²-pyrophosphates of this invention can be derived from the literature cited in U.S. Pat. No. 4855304 which discloses some dinucleoside pyrophosphates and pyrophosphate homologs useful for inhibiting plant virus replication.

In a representative embodiment of this invention, the above described reaction pathway is carried out essentially under the conditions described by A. M. Michelson, that is, the nucleoside phosphate of the formula (II) or a salt thereof, (e.g. the sodium, litium, or barium salt) is first transformed into the corresponding salt with a hindered tertiary amine base such as tri-n-butylamine or tri-n-octylamine, or with a hindered quaternary ammonium base such as methyl-tri-n-octylammonium hydroxide. The transformation is usually performed via the intermediate formation of a pyridinium salt by elution of the nucleoside phosphate or a salt thereof (preferably the sodium salt) through an ion-exchange (strong cationic) resin in the pyridinium form. This step has mainly the purpose of eliminating sodium or other mineral cations. The pyridinium salt is then incubated with a methanol solution containing an equimolar amount of the hindered tertiary amine base and then dried under reduced pressure to yield the salt with hindered tertiary amine base. The salt of the nucleoside phosphate of formula (II) is then contacted with an excess (1.5 to 2.5 mole per mole of nucleoside phosphate) of the activating agent (e.g. diphenyl phosphocloridate or tetraphenyl pyrophosphate) in the presence of an excess of an acid acceptor (1.2 to 2 mole per mole of activating agent) which does not interfere with the reactants, e.g. a tertiary aliphatic amine (e.g. tri-n-butylamine) or a tertiary heterocyclic amine (e.g. N-methylpiperidine, N-methylpyrrolidine). The activation reaction is generally carried out at room temperature and under anhydrous conditions by employing as a solvent an inert aprotic organic solvent such as a cyclic ether (e.g. dioxane) or a mixture thereof. In some cases, addition of a further inert organic solvent of high solubility power (e.g. dimethylformamide) is advisable to increase the concentration of the reactants and, therefore, the reaction speed.

Under the above conditions, the formation of the activated phosphate ester is usually completed within 2 to 5 hours.

The activated phosphate ester is then reacted with a salt of the nucleoside phosphate (III) with a hindered tertiary amine base or quaternary ammonium hydroxide such as those exemplified above, in the presence of an inert organic aprotic solvent, e.g. pyridine, hexamethylphosphoramide, dimethylformamide or a mixture thereof. The reaction is usually carried out at a temperature ranging between 20° C. and 35° C. and it is completed in a period of time of 15 to 30 hours.

The crude reaction product is usually recovered by evaporation of the solvent under reduced pressure and then submitted to common purification procedures, including chromatographic methods. For instance, for the purification procedure of those compounds of formula (I) wherein R and/or $R_1$ are(is) hydrogen, the crude product is then suspended in water and, after adjustment of the value of the pH to 8 with an aqueous alkali metal hydroxide, the solution is extracted with an aprotic organic solvent non-mixable with water, such as diethyl ether. The aqueous phase containing the dinucleoside pyrophosphate is submitted to further purification by combining column chromatography methods (e.g. by using a gel filtration column and water as the eluent) and HPLC methods (e.g. by using a linear hydrocarbons functionalized silica gel reverse phase column and eluting with a linear gradient of methanol in water or a strong anion exchange resin and eluting with a linear gradient of lithium chloride in water).

The dinucleoside-5',5'-P¹,P²-pyrophosphates of formula (I) of this invention are in general stable compounds, in particular, when isolated under the form of salts with biologically acceptable cations, e.g. as sodium or potassium salts. Therefore, although when R and/or $R_1$ represent(s) hydrogen, they may be isolated and characterized in the form of free acids, (e.g, by loading an aqueous solution of the salt on an ion exchange resin in the H⁺ form and eluting the resin with water or a mixture of methanol and water), they are preferably stored or utilized in the form of salts, most preferably, as salts with biologically acceptable cations.

The non-naturally occurring nucleoside phosphates starting materials

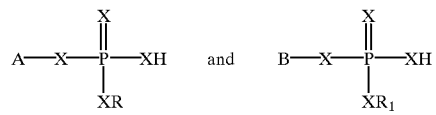

can be prepared according to standard procedures from the corresponding non-phosphorylated nucleosides.

Example of such non-phosphorylated precursors which are described in the state of the art are the following;
thymine-3'-azido-2',3'-dideoxy-D-riboside (AZT), adenine-2',3'-dideoxy-D-riboside (DDA), 5-fluorouracil-2'-deoxy-D-riboside (FDU), cytosine-2',3'-dideoxy-D-riboside (DDC), uracil-3'-azido-2',3'-dideoxy-D-riboside (AZDDU), hypoxanthine-2',3'-dideoxy-D-riboside (DDI), and guanine-2',3'-dideoxy-D-riboside (DDG). See the following references: Levene P. A., J. Biol. Chem., (1929), Vol. 83, 793; Davoli J. et al., J. Chem Soc. (1948), 967; Howard G. A. et al., J. Chem Soc. (1947), 1052; Robins M. J. et al., J. Am. Chem. Soc. (1971), 93:20, 5277; Chu C. K. et al., J. Org. Chem. (1989), 54, 2217; Colla L. et al., Eur. J. Med. Chem. Chim. Ther., (1985), No. 4, 295.

In most cases the above precursors, are also available on the market (e.g. from SIGMA Chemical Co., St. Louis, Mo., USA).

Methods for converting the non-phosphorylated precursor to the corresponding phosphorylated compound are also known from the state of the art. A typical procedure for the preparation of the monophosphates of the nucleosides consists in contacting the nucleoside with a solution of cyanoethyl phosphate in anhydrous pyridine in the presence of a condensing agent such as dicyclohexylcarbodiimide at room temperature. The final products may be conveniently recovered and purified under the form of salts with alkaline or alkaline earth metals such as sodium, litium or barium salts.

In some cases, the nucleoside monophosphates are available on the market (e.g. 5-fluoro-2'-deoxyuridine-5'-monophosphate, SIGMA Chemical Co. St. Louis, Mo., USA).

The compounds of formula (I) have antiviral (including anti-HIV) and/or antitumoral activity and are useful as active ingredients of pharmaceutical compositions.

To confirm the anti-HIV activity of some dinucleoside-5',5'-P¹,P²-pyrophosphates representative of this invention, in vitro tests have been carried out on a HTLV-1 transformed cell line, MT-4, which is highly susceptible to and permissive for HIV infection. The inhibition of the HIV-induced cytopathic effect was used as the end point. The procedure of this test is essentially that described by R. Pauwels et al.

"Rapid and automated tetrazolium-based calorimetric assay for the detection of anti-HIV compounds". Journal of Virological Methods, 20, (1988), 309–321.

The following Table II shows the 50% effective concentration (IC50) and the 50% cytotoxic concentration (CC50) for the di-(thymine-3'-azido-2',3'-dideoxy-D-riboside)-5',5'-$P^1,P^2$-pyrophosphate (di-AZT-5',5'-$P^1,P^2$-pyrophosphate). Thymine-3'-azido-2',3'-dideoxy-D-riboside (AZT) was taken as control compound.

TABLE II

Anti-HIV in vitro activity

| COMPOUND | IC50 ($\mu M$) | CC50 ($\mu M$) |
|---|---|---|
| di-AZT-5',5'-$p^1,p^2$-pyrophosphate (Compound 1, Table I) | 0.031 | >100 |
| AZT | 0.028 | 70 |

The compounds of this invention are particularly useful as pro-drugs to be carried by erythrocytes to specific cellular populations where they can be rapidly converted in vivo to the active form.

Erythrocytes offer a unique opportunity as biological carriers of drugs or pro-drugs because;

(a) they have a rather simple metabolism and, therefore, a relatively limited set of enzymes which may interact with the encapsulated drug or pro-drug, (b) they can reach all parts of the body and may act as bioreactors for the transformation of the encapsulated drug or pro-drug into the active form according to controlled kinetics which may be programmed on the basis of the characteristics of the enzymes involved, and (c) are fit for relatively simple modifications which may confer a site-specific targeting to tissues and organs which are rich in blood cells.

It is known that the active forms of some nucleoside drugs are the phosphorylated derivatives. In particular, it is commonly accepted that the triphosphorylated derivatives are the forms which are responsible of the inhibition of the viral replication by the deoxy-nucleosides having anti-HIV activity. However, the triphosphorylated deoxy-nucleosides are not clinically useful since they cannot pass through the cell membranes. Therefore, a critical factor of the anti-HIV deoxy-nucleosides effectiveness is how easily they can enter the target cell and undergo phosphorylation by cellular enzymes.

Anyhow, it is known that nucleosides may undergo not only intracellular phosphorylation but also other reactions may be promoted by intracellular enzymes which transform the nucleosides into less therapeutically active or even inactive compounds. If the rate of these reactions has the same order as that of the phosphorylation process, then the therapeutical effectiveness of the nucleosides is lowered. These considerations are particularly important since some target cells (e.g. macrophages) have low levels of phosphorylating enzymes and therefore administration of antiviral nucleosides in the phosphorylated form to said infected cells may present remarkable advantages in terms of viral inhibition over the conventional administration route.

One of the aims of this invention is that of exploiting the capability of the dinucleoside-5',5'-$P^1,P^2$-pyrophosphates of being encapsulated into blood red cells and to be carried specifically to the target cells where an enzymatic pathway is available that cleaves the pyrophosphate bond yielding two nucleotides. The two nucleotides already containing a phosphorylated moiety are in the proper chemical form to carry out the desired biological function or to be rapidly converted into the active form of triphosphorylated derivatives, without being substantially inactivated.

The dinucleoside pyrophosphates are more suitable than the corresponding monophosphates for encapsulation and targeting technology in that, once they are introduced into the erythrocytes, they are more stable and show a lower diffusion rate from the erythrocyte's membrane during the period between the time of encapsulation and the time of site-specific delivery of the pro-drug. These characteristics allow more flexibility in programming the kinetic of the release of the nucleoside from its carrier.

A further advantage of the dinucleoside-5',5'-$P^1,P^2$-pyrophosphates is that it is possible to combine through the pyrophosphate bonding different pairs of nucleosides showing complementary or synergic action and having both nucleosides introduced into the carriers, delivered to the specific target cells and released in the respective active forms, simultaneously, during each of such steps.

Typical target cells for the encapsulated dinucleoside-5',5'-$P^1,P^2$-pyrophosphates are the macrophages or the hepatic and splenic body districts. Methods for targeting manipulated erythrocytes to the reticuloendothelial system have been described for instance by Zocchi E. et al., in "Hepatic or splenic targeting of carrier erythrocytes: A murine model", Biotechnology and Applied Biochemistry (1987), 9, 423–434 and in the paper by Tonetti M. et al., mentioned above. These methods allow the target cell or body districts to recognize the biological carriers and to interact with them in order to provoke the site specific and pharmacokinetically controlled drug release.

The encapsulation of antitumor drugs and pro-drugs in suitable biological carriers such as erythrocytes, has been proposed as a useful mean to achieve a selective organ targeting to slow release of therapeutic agents with positive effects on both therapeutic responses and toxicity (Zocchi E. et al., in Proc. Natl. Acad. Sci. USA (1989) Vol. 86, 2040–2044). An example of encapsulation of the 5-fluorouracil-2'-deoxy-D-riboside-5'-monophosphate pro-drug into erythrocytes (see: De Flora A. et al., Proc. Natl. Acad. Sci. USA, (1988), Vol. 85, 3145–3149) shows that to achieve a pharmacokinetically useful control of the release of the active non-phosphorylated drug, co-encapsulation of equimolar amounts of other nucleoside triphosphates is required.

The co-entrapment of other nucleotides may involve problems of biological compatibility and of interaction between the selected nucleoside pro-drug and the accompanying nucleoside triphosphate. One of the advantages provided by this invention, consists in the possibility of preparing 5-fluorouracil pro-drugs which do not require the co-entrapment of other nucleoside triphosphates to achieve the appropriate pharmacokinetic control.

A representative example of the pro-drugs of this invention showing useful pharmacokinetic characteristics, is a dinucleoside-5',5'-pyrophosphate consisting of two units of 5-fluorouracil-2'-deoxy-D-riboside linked through a pyrophosphate bond [di-(5-fluorouracil-2'-deoxy-D-riboside)-5',5'-$P^1,P^2$-pyrophosphate] which shows a lower de-phosphorylation rate with respect to the respective monophosphate.

A typical example of encapsulation of a dinucleoside-5',5'-$P^1,P^2$-pyrophosphate representative of this invention in human red blood cells, was performed with di-AZT-5',5'-$P^1,P^2$-pyrophosphate by the hypotonic dialysis and isotonic releasing method (De Flora A. et al., Proc. Natl. Acad. Sci. USA, (1988), Vol. 85, 3145–3149). A two step procedure was used consisting of a first dialysis of the washed and packed erythrocytes (80% hematocrit) against 70 volumes of hemolysing buffer (5 mM $Na_2HPO_4$ supplemented with 4 mM $MgCl_2$, pH 7.2, 26 mOsm) for 35 minutes at 4° C. under gentle rotation. This step was followed by addition of 10–15 mM di-AZT-5',5'-$P^1$,$P^2$-pyrophosphate inside the dialysis bag and further dialysis for 15 minutes under the same conditions. Erythrocytes were then resealed by dialysing them for 40 minutes at 4° C. against phosphate-saline buffer, pH 7.4, supplemented with 10 mM glucose and adenosine, 310 mOsm. The loaded erythrocytes were then extensively washed with ice-cold aqueous NaCl (0.9% w/w) and incubated at 37° C. in autologous plasma at 10% hematocrit.

The concentration of the dinucleoside pyrophosphate and its metabolites in the plasma and red blood cells was determined at successive time intervals by using the following method.

At various times, 1 ml aliquots of the incubation mixture were withdrawn. After the separation of the erythrocytes from plasma, the two fractions were separately extracted.

100 Microliters of packed red blood cells (RBC) were added to 100 microliters of water, then 68 microliters of 3.7M perchloric acid (PCA) were added under vigorous shaking. The sample was centrifuged and 140 microliters of the supernatant were neutralized with 30 microliters of 3M potassium carbonate. The sample was then centrifuged to remove the formed precipitate.

150 Microliters of the plasma fractions were treated with 50 microliters of 3.7M PCA and 120 microliters of the supernatant were neutralized with 27 microliters of 3M potassium carbonate and centrifuged. 5 Microliters of each extraction were injected into a HP 1090 instrument (Hewlett-Packard, Palo Alto, Calif.) equipped with a HP ODS Hypersil 4.6×60 mm 3 micron particle size column. The solvent program was a linear gradient starting at 100% of buffer A (0.1M $KH_2PO_4$ with 5 mM tert-butylammonium hydroxide (TBA), pH 4.9) and increasing up to 100% buffer B (0.1M $KH_2PO_4$ with 5 mM TBA, in 40% (v/v) methanol in water, pH 4.9) in 30 minutes; 100% buffer B was maintained up to 50 minutes. The flow rate was 0.4 ml/min and the eluted compounds were monitored with a spectrophotometric detector set at 265 nm. Retention times for the various compounds were (in minutes): AZT, 17; AZT-monophosphate, 21; di-AZT-pyrophosphate, 33.

The following Tables III and IV report the results of the above described determinations.

TABLE III

Concentration of di-AZT-5',5'-$P^1$,$P^2$-pyrophosphate and its metabolites into human red blood cells, expressed in µmoles/ml

| Time (h) | Di-AZT-pyrophosphate | AZT-monophosphate | AZT |
|---|---|---|---|
| 0 | 3.9 | 0.04 | — |
| 2 | 4.1 | 0.09 | — |
| 6 | 2.9 | 0.65 | 0.60 |
| 24 | 1.8 | 0.93 | 0.10 |

TABLE IV

Concentration of di-AZT-5',5'-$P^1$,$P^2$-pyrophosphate and its metabolites in human plasma, expressed in nmoles/ml

| Time (h) | Di-AZT-pyrophosphate | AZT-monophosphate | AZT |
|---|---|---|---|
| 0 | 4.49 | 21.94 | 4.6 |
| 2 | 3.75 | 28.21 | 14.42 |
| 6 | 5.27 | 24.68 | 62.43 |
| 24 | 5.34 | 67.11 | 355.78 |

The above data show that the di-AZT-5',5'-$P^1$,$P^2$-pyrophosphate concentration in the human red blood cells attains a value which is compatible with the therapeutical requirements according to the current practice and that the drug is released from the erythrocytes at a very low rate. The above described characteristics make the engineered erythrocytes, containing an anti-HIV effective amount of the dinucleoside phosphate pro-drug, particularly useful for therapeutical purposes. It is in fact known that human erythrocytes may be suitably modified to encapsulate nucleoside drugs and to impart specific targeting properties and that such modifications do not alter the physiological behavior of the erythrocytes apart from the selective targeting features (International Patent Application Publication No. WO 92/22306).

The estimate of the concentration of the dinucleoside pyrophosphate in the erythrocytes which corresponds to therapeutical effectiveness when they are targeted to HIV-infected cells, such as macrophages, is made on the basis of the data reported by B. L. Robbins et al., in Antimicrobial Agents and Chemotherapy, Vol. 38, No. 1, (1994) 115–121. In fact, these authors show that in HIV infected patients under effective treatment with AZT, the intracellular concentration of the AZT triphosphate in peripheral blood mononuclear cells (PBMCs) ranges from $5.10^{-15}$ mol/$10^6$ cells to $9.10^{-14}$ mol/$10^6$ cells. These values are clearly overcome when at least one erythrocyte containing dinucleoside pyrophosphate at the concentration value indicated in Table III (which correspond to about $2.10^{-10}$ mol/$10^6$ cells to $4.10^{-10}$ mol/$10^6$ cells) is captured by a PBMCs (e.g. a monocyte or a macrophage).

As described above, the dinucleoside-5',5'-$P^1$,$P^2$-pyrophosphates of this invention can be utilized as active ingredients of pharmaceutical compositions for oral or parenteral route administration or can be utilized as active drugs or pro-drugs encapsulated into biological carriers targeted to specific body districts (e.g. liver/spleen) and/or cell populations (e.g. monocytes/macrophages).

When the dinucleoside-5',5'-$P^1$,$P^2$-pyrophosphates are utilized as active ingredients of pharmaceutical compositions for oral or parenteral administration, said compositions usually comprise a therapeutically effective amount of the dinucleoside pyrophosphate and an inert carrier and/or diluent. For instance, in liquid pharmaceutical compositions for oral administration, water, preferably, sterilized water, may be used as a carrier and/or diluent. Solid pharmaceutical compositions for oral administration may contain binders, disintegrating agents and lubricants. As an example, gelatin, gum tragacanth or microcrystalline cellulose may be used as binders, alginic acid or corn starch may be used as disintegrating agents; magnesium or calcium stearate may be used as lubricant. Certain solid forms, such as capsules, may contain a liquid carrier, for instance, a fatty oil. For parenteral administration forms, a preferred carrier and/or diluent may be physiological saline or phosphate buffered saline. The liquid pharmaceutical compositions for both oral and parenteral administration may include also other compatible components, such as solvents, preservatives, and/or adjuvants, for instance: polyethylene glycols, propylene glycols or glycerine as solvents, methylparabens as antibacterial agents, ascorbic acid or sodium bisulfide as antioxidants, ethylenediaminetetraacetic acid as a chelating agent, acetates, citrates or phosphates as buffering agents. Moreover, other active ingredients which do not impair the desired effect of the dinucleoside pyrophosphates may be incorporated into the pharmaceutical formulations.

The oral or parenteral pharmaceutical compositions in general should be able to provide serum concentrations in patients which range from 0.1 to 3.0 μM. It is, anyhow, possible to apply dosages outside this range, being understood that the daily dosage must be adjusted according to the type and severity of the disease, the status of the patient to be treated and the specific dinucleoside pyrophosphate employed.

Tablets, pills, capsules, troches and the like, may be used as the solid dosage forms for oral administration, while solutions, suspensions, elixirs and syrups are preferably utilized as liquid dosage forms. The parenteral formulations are usually consisting of solutions for subcutaneous injections or for intravenous administration.

The unit dosage forms may generally contain from 10 to 500 mg of dinucleoside-5',5'-$P^1$,$P^2$-pyrophosphate, this indication having a purely exemplary character and being in no way limiting the scope of the invention.

When the dinucleoside-5',5'-$P^1$,$P^2$-pyrophosphates of this invention are utilized as drugs or pro-drugs encapsulated into suitable biological carriers, the pharmaceutical compositions which contain such dinucleoside pyrophosphates preferably comprise transformed erythrocytes. The surface of such transformed erythrocytes is modified in order to be specifically recognized by the cells of the organism in which the dinucleoside pyrophosphates contained in such erythrocytes are to be integrated. For instance, a typical way to achieve said specific recognition by cells hosting human or animal pathogenic RNA-type viruses is described in European Patent Application Publication No. 517986 and is essentially based on binding to the surface proteins and/or transmembrane proteins of the erythrocytes, prior to or after the encapsulation of the dinucleoside pyrophosphates, specific antibodies which can be recognized by phagocytes (e.g. lymphocytes, monocytes or macrophages) that successively engulf the red cells. According to a preferred embodiment, the erythrocytes, after loading with the dinucleoside-5',5'-$P^1$,$P^2$-pyrophosphates, are treated first, with a reversibly clustering agent of the surface or transmembrane proteins, then, with a covalently linking cross-linking agent and, finally, are incubated in autologous plasma to bind IgG molecules. These erythrocytes are recognized by human macrophages through their receptors and then phagocytized in a ratio of about 1 erythrocyte per macrophage.

The following experiments describe in detail the targeting of di-AZT-pyrophosphate loaded erythrocytes to human macrophages.

Human erythrocytes submitted to the procedure of di-AZT-pyrophosphate loading described above were then modified to increase their recognition by macrophages. The procedure is described in detail in EP-A-517986. The di-AZT-pyrophosphate loaded erythrocytes were found to show about 1,500 IgG molecules/cell and be phagocytosed more efficiently than non-treated erythrocytes as shown in Table V. The number of IgG bound/cell was determined by incubation of 50 μl RBC with 100 μl of 5 mM HEPES in PBS, pH 7.4, containing 4% (w/v) bovine serum albumine and 0.1 mCi of radioiodinated protein A (specific activity 30 mCi/mg protein). The samples were incubated for 30 min at room temperature and then washed four times and counted for bound radioactivity in a Beckman 5500 γ-counter. Phagocytosis of drug-loaded erythrocytes was determined in vitro as described in the paper by m. Magnani et al. "Targeting antiretroviral nucleoside analogues in phosphorylated form to macrophages: in vitro and in vivo studies", (1992) Proc. Nat. Acad. Sci. USA, 89; 6477–6481.

TABLE V

Recognition of di-AZT-pyrophosphate loaded erythrocytes by macrophages

| | Native | Di-AZT-pyro-phosphate loaded | Di-AZT-pyro-phosphate loaded plus $ZnCl_2/BS^3$ |
|---|---|---|---|
| IgG bound (molecules/cell) | 20–40 | 20–40 | ≃1,500 |
| Phagocytosis (erythrocytes/macrophage) | 0.1–0.2 | 0.1–0.2 | >1 (1–1.2) |
| Di-AZT-pyrophosphate in macrophages | N.D. | N.D. | 3 pmoles/$10^6$ cells |

N.D.: not detectable

The amount of di-AZT-pyrophosphate delivered by carrier erythrocytes to macrophages and its stability in macrophages was also evaluated. Human erythrocytes were loaded with di-AZT-pyrophosphate at a concentration of 0.4 μmoles/ml RBC and then modified to increase their recognition by macrophages as above. Modified erythrocytes were added to macrophages at a ratio of 100 RBC per macrophage and phagocytosis was for 24 h. Non ingested RBC were then washed extensively (three times) with RPMI 1640 medium and once washed with 0.9% (w/v) ammonium chloride. Macrophages perchloric acid extracts were then prepared at time 0 and 24, 48 or 72 h after RBC phagocytosis and neutralized with $K_2CO_3$. The extracts were then neutralized and processed for solid-phase extraction of di-AZT-pyrophosphate by using Isolute™ C18 columns (from International Sorbent Technology, Mid-Glamorgan, UK) according to the instructions from manufacturer and employing methanol as the eluent. The extracts were analyzed by HPLC as described above. The results on di-AZT-pyrophosphate stability in human macrophages are shown in FIG. 1.

Assay of the antiviral activity of di-AZT-pyrophosphate loaded erythrocytes on feline monocyte-derived macrophages infected with feline immunodeficiency virus (FIV) was also performed.

Feline monocyte-derived macrophages were cultured as reported for human monocyte-derived macrophages by M. Magnani et al. "Targeting antiretroviral nucleoside analogues in phosphorylated form to macrophages; in vitro and in vivo studies", (1992) Proc. Natl. Acad. Sci. USA, 89: 6477–6481. Di-AZT-pyrophosphate loaded erythrocytes were added for 15 h at a ratio of 100 RBCs per macrophage. The di-AZT-pyrophosphate content of drug-loaded erythrocytes was 0.4 μmoles/mi RBCS. Non-ingested erythrocytes were removed with extensive washing. As a control macrophage cultures were treated with "unloaded" erythrocytes (i.e. erythrocytes submitted to the same procedure but without addition of di-AZT-pyrophosphate.

Macrophage cultures receiving di-AZT-pyrophosphate loaded RBCs, "unloaded" RBCs or no addition were infected with 330 i.d./well of feline immunodeficiency virus (Pisa M-2) as described in the paper by M. Bendinelli et al. "Feline immunodeficiency virus: and interesting model for AIDS studies and an important cat pathogen", (1995), Clin. Microbiol., rev. 8: 87–112. Cell cultures were extensively washed (six times) to remove any viral particle associated with macrophages 8 h after infection. Cell cultures were then maintained at 37° C., 5% $CO_2$ for three days and then their total DNA was isolated. DNA isolation from macrophages was obtained by standard techniques which include cell lysis with 8M urea, 0.3M NaCl, 10 mM Tris HCl, pH 7.5, for 60 min at 37° C. Extraction was with phenolchloroform-isoamyl alcohol (25:24:1 v/v/v) and DNA precipitation was with ethanol. Analysis of FIV proviral DNA was performed by amplification of 498 base pairs of the viral p24 gag gene in two stages. For the first stage of amplification, the following primers were used: 5'-GGCATATCCTATTCAAACAG-3' (sense) (SEQ ID No:1) corresponding to nucleotides 1025–1044 in the viral sequence and 5'-CCTATATTTTACGTTGAGAA-3' (antisense) (SEQ ID No:2) corresponding to nucleotides 1680–1699. For the second stage of amplification the primers used were: 5'-TATGGTTTACTGCCTTCTCT-3' (sense) (SEQ ID No:3) corresponding to nucleotides 1141–1160 in the viral sequence and 5'-GAATTCGGTCTTTCATGGGA-3' (antisense) (SEQ ID No:4) corresponding to nucleotides 1619–1638.

PCR, performed in a Perkin-Ewas thermocycler, was done in 50 $\mu$l final volume containing 168 ng of genomic DNA, 50 mM KCl, 10 mM Tris HCl, pH 8.3, 1.5 mM $MgCl_2$, 0.005% Tween-20, 0.005% NP-40, 0.001% gelatin, 150 nM each of the primer and 5 U of Replitherm DNA polymerase (Epicentre Technologies, Madison, Wis., U.S.A.). The reaction mixture containing the first pair of primers, was subjected to 40 cycles of denaturation at 94° C. for 1 min, annealing at 50° C. for 1 min, and extension at 72° C. for 2 min followed by final extension at 72° C. for 15 min. Then, 10 $\mu$l of this amplified mixture was re-amplified with the second pair of primers using exactly the same conditions.

The PCR products were analyzed by electrophoresis on 1.5% agarose gel, transferred onto nylon membrane and hybridized with a 498 bpair of the p24 gag gene probe cloned in a TA-cloning plasmid (Invitrogen Corporation, San Diego, Calif., U.S.A.). As an internal control the feline hexokinase gene was amplified with the following primers:

5'-ACATGGAGTGGGGGGCCTTTGG-3' (sense) (SEQ ID No:5) corresponding to nucleotide 2198–2219 and
5'-GTTGCGGACGATTTCACCCAGG-3' (antisense) (SEQ ID No:6) corresponding to nucleotide 2328–2349 in the human hexokinase type I cDNA. Detection was with a FIV hexokinase probe.

The results are shown in FIG. 2.

A further assay of antiviral activity of di-AZT-pyrophosphate loaded erythrocytes was performed on murine macrophages infected with the murine immunodeficiency virus.

Murine macrophages were obtained from the peritoneal cavity of C57BL/6 mice and cultured as described in the paper by Rossi et al. "Inhibition of murine retrovirus-induced immunodeficiency disease by dideoxycytidine and dideoxycytidine 5'-triphosphate", (1993), J. AIDS, 6: 1179–1186. Di-AZT-pyrophosphate loaded erythrocytes and infection were as described for FIV with the following modifications: the murine immunodeficiency virus (LP-BM5) was prepared as a cell-free supernatant from SC-1 cells according to standard procedures (D. E. Yetter et al. "Functional T-lymphocytes are required for a murine retro-virus induced immunodeficiency disease (MAIDS)", (1987), J. Exp. Med. 165:1737–1742).

PCR analysis of viral DNA was performed according to the following procedure.

The following oligonucleotide primers were used for the amplification of defective virus genome (BM5d): 5'-primer, 5'-AACCTTCCTCCTCTGCCA-3' (sense) corresponding to nucleotides 1456–1473 in the viral sequence and 3'-primer, 5'-ACCACCTCCTGGGCTTTC-3' (antisense) corresponding to nucleotides 1579–1596 of the BM5d genome. A second pair of oligonucleotide primers were used for the amplification of a 203 bp of a mouse G6PD gene. This amplification served as an internal control (endogenous standard) for the evaluation of relative BM5d integration in the mouse genome.

The nucleotide primers for this amplification were 5'-primer, 5'-TGTTCTTCAACCCCGAGGAT-3' (sense) and 3'-primer, 5'-AAGACGTCCAGGATGAGGTGATC-3' (antisense).

The four primers used herein are described in the paper by G. Brandi et al. "Efficacy and toxicity of long-term administration of 2',3'-dideoxycytidine in the LP-BM5 murine induced immunodeficiency model", (1995), Antiviral Chemistry and Chemotherapy, 6, 153–161.

PCR, performed in a Perkin-Elmer thermocycler, was done in 25 $\mu$l final volume containing 0.229 $\mu$g of genomic DNA, corresponding to about 114,000 cells, 50 mM KCl, 10 mM Tris-HCl, pH 8.3, 1 mM$MgCl_2$, 0.05% Tween-20, 0.005% NP-40, 0.001% gelatin, 150 $\mu$M each of the four deoxyribonucleoside triphosphates, 20 pmoles of each primer and 2.5 U of Replitherm DNA polymerase (Epicentre Technologies, Madison, Wisc., U.S.A.). The reaction mixtures were subjected to 37 cycles of denaturation at 95° C. for 30 sec, annealing at 58° C. for 30 sec, and extension at 72° C. for 30 sec followed by final extension at 72° C. for 10 min. The PCR products were analyzed by electrophoresis on 2.5% agarose gel, transferred onto nylon membrane and hybridized with either the 32P-labelled D30 or G6PD probe. Labelling of the DNA probes was by the random primer DNA-labelling kit from Bio-Rad (Bio-Rad Laboratories, Hercules, Calif., U.S.A.). The results are shown in FIG. 3.

The pharmaceutical compositions containing modified erythrocytes entrapping the dinucleoside pyrophosphates of this invention are usually presented under the form of isotonic solutions, such as saline or glucose isotonic solutions, for injectable use or in a form to be used for the extemporaneous preparation of injectable solutions for intravenous or intraperitoneal administration.

These pharmaceutical compositions usually contain an amount of erythrocytes which varies preferably from 2 to 8 ml and a total amount of dinucleoside-5',5'-$P^1$,$P^2$-pyrophosphates that varies from about 0.5 to about 10 mM. The dosage at which the encapsulated dinucleoside pyrophosphates of this invention may be administered ranges from about 0.5 to about 80 $\mu$g of dinucleoside pyrophosphates per kilogram of body weight of the patient, being understood that these values are given as an indication which is not intended to constitute a limitation of the scope of the invention.

EXAMPLE 1

Figure 1:
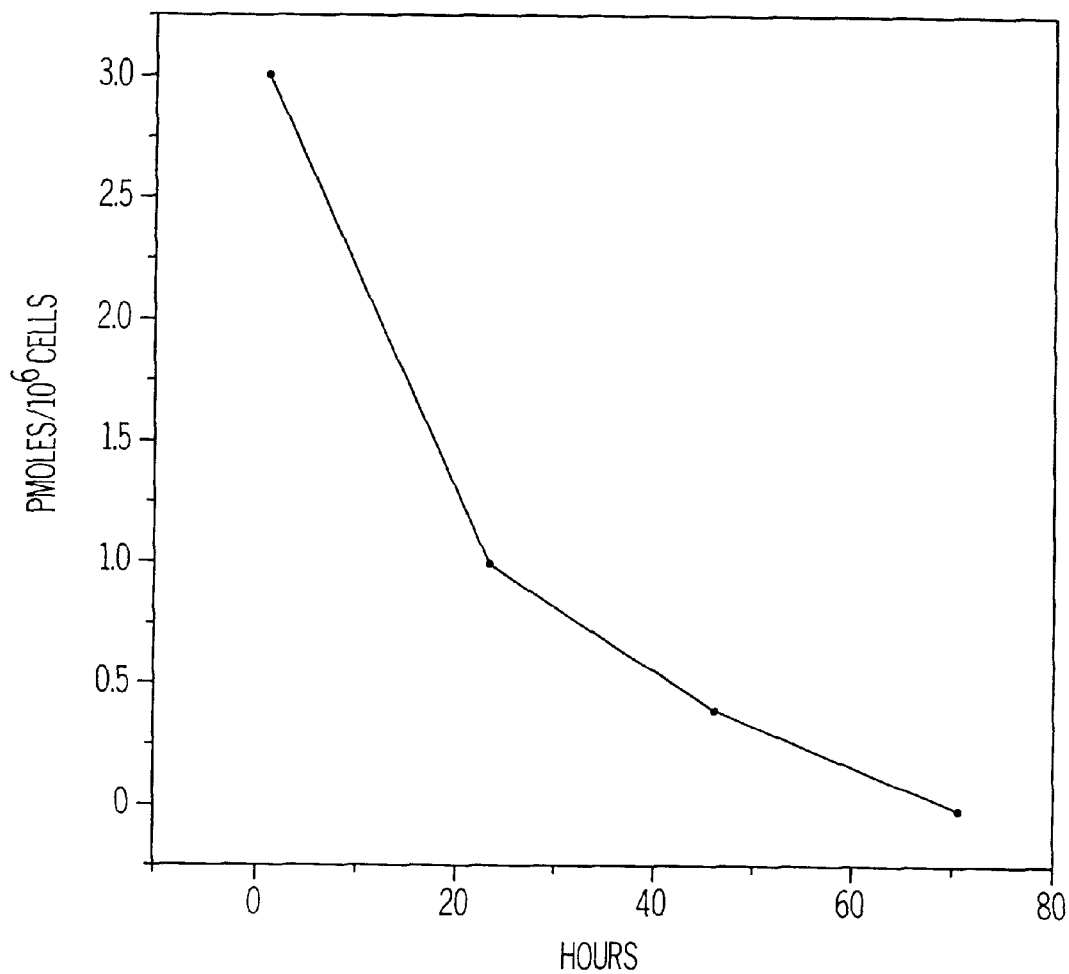
FIG. 1 shows the stability of di-AZT-pyrophosphate in human macrophages.
Figure 2:
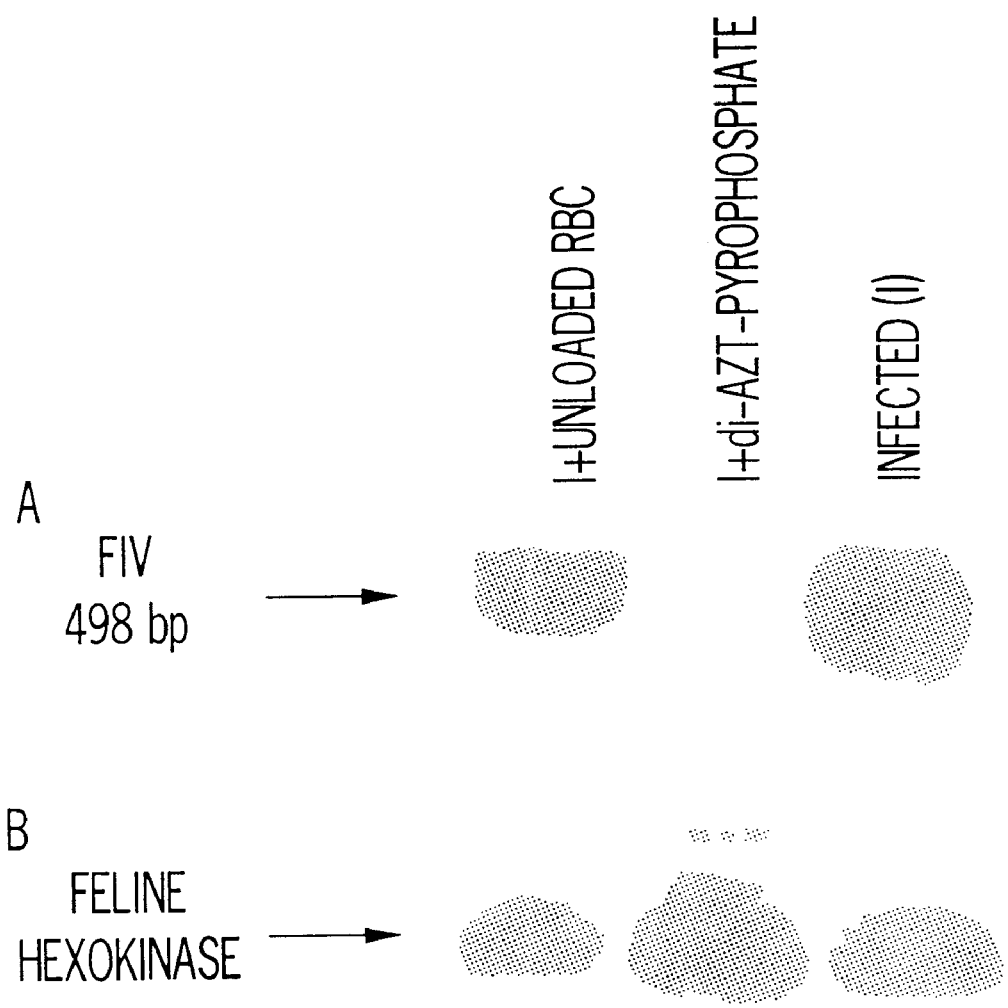
FIG. 2 shows the antiviral activity of di-AZT-pyrophosphate loaded erythrocytes against feline monocyte-derived macrophages infected with FIV (Pisa M-2) measured by analysis of FIV proviral DNA in macrophages.
Figure 3:
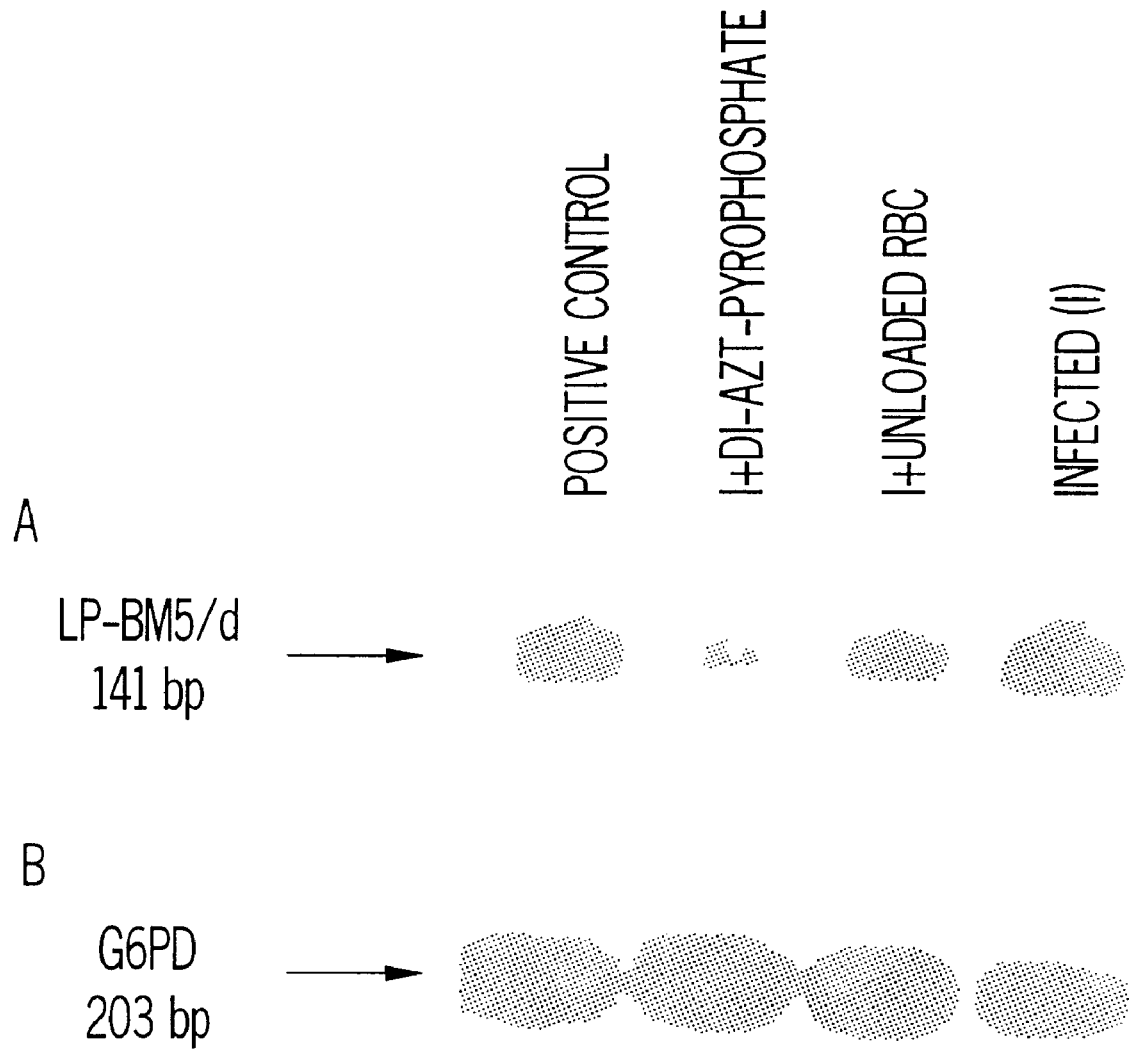
FIG. 3 shows the antiviral activity of di-AZT-pyrophosphate loaded erythrocytes against murine macrophages infected with murine immunodeficiency virus (LP-BM5) measured by analysis of defective virus genome (BM5d) DNA.

Preparation of hypoxanthine-2',3'-dideoxy-D-riboside-5'-monophosphate 100 mg (0.4 mmoles) of hypoxanthine-2',3'-dideoxy-D-riboside were added to 0.11 ml (1.2 mmoles) of phosphorus oxychloride in 1 ml triethyl phosphate and the mixture was stirred for 2 hours at −5° C. The mixture was extracted four times with 10 ml of ice-cold diethyl ether, then, it was centrifuged at 2000 rpm for 5 minutes at 0° C. After removal of diethyl ether, the residue was suspended in 5 ml of water at 0° C. and immediately neutralized with cold 1N NaOH. The mixture was kept on an ice bath for 10 minutes and the pH value was adjusted to 7. After drying under vacuum, the residue was dissolved in 25 ml of methanol. The solution was applied to a column containing 35 g of silica gel suspended in diethyl ether. The pure title compound was obtained by eluting the column as follows (flow rate 3 ml/min.): 150 ml diethyl ether, 150 ml of a mixture diethyl ether:methanol 60:40 (v/v), to wash off all the impurities and, finally, about 300 ml of methanol to elute the purified product.

The yield of the total process was 85%.

The MS-spectrum recorded with a Hewlett-Packard 5989A instrument shows a molecular ion at m/z 315.2 corresponding to the [M-1]− ion of the compound of the title.

EXAMPLE 2

Preparation of thymine-3'-azido-2',3'-dideoxy-D-riboside-5'-monophosphate 240 mg (1 mmole) of thymine-3'-azido-2',3'-dideoxy-D-riboside (AZT) were dissolved in 2 ml of a 1M cyanoethyl phosphate solution in pyridine and vacuum dried at 30° C. The residue was suspended in 19 ml of anhydrous pyridine and then vacuum dried at 30° C., twice. After addition of 9.6 ml of anhydrous pyridine and 1.15 g of dicyclohexylcarbodiimide, the mixture was stirred for 48 hours at 25° C. Then, 2.8 ml of water were added and the solution was stirred for further 30 minutes at 25° C. and finally vacuum dried at 30° C. The residue was suspended in 9.6 ml of water, filtered and washed again on filter with 9.6 ml of water. Then, 19.6 ml of 1N NaOH were added to the combined filtrates and the mixture was heated under reflux for 40 minutes.

The solution was cooled to 25° C. and eluted through a column filled with 15 g of Dowex® 50 (H+) ion exchange resin in order to remove the sodium cation. The pH of the eluate was adjusted to 7.5 with a saturated solution of $Ba(OH)_2$ in order to precipitate the phosphate anion. After centrifugation, the supernatant was reduced to a small volume (30 ml) under vacuum at 30° C. and centrifuged again to eliminate the residual inorganic phosphate. A double volume of ethanol was added to the mixture at 4° C. to precipitate the barium salt of the title compound. The precipitate was finally washed with acetone and diethyl ether and dried under a gentle stream of nitrogen.

The barium salt of the title compound was suspended into 5 ml of water and mixed with 2 g of Dowex® 50 (H+) ion exchange resin. The mixture was then applied to a column containing 2 g of Dowex® 50 (H+) ion exchange resin. The column was eluted with 30 ml of a mixture methanol:water 1:1 (v/v), and the eluate was finally neutralized with 1N NaOH and the solution containing the sodium salt of AZT-5'-monophosphate was then lyophilized giving the sodium salt of the product of the title in a 70% yield.

The MS-spectrum recorded with a Hewlett-Packard 5989A instrument shows a molecular ion at m/z 346.50 corresponding to the [M-1]− ion of the compound of the title.

EXAMPLE 3

Preparation of thymine-3'-azido-2',3'-dideoxy-D-riboside, hypoxanthine-2',3'-dideoxy-D-riboside-5', 5'-p1-$P^2$-pyrophosphate a) Activation of hypoxanthine-2',3'-dideoxy-Driboside-5'-monophosphate 50 mg (0.016 mmoles) of hypoxanthine-2',3'-dideoxy-D-riboside-5'-monophosphate were dissolved into a mixture of 2 ml of water and 1 ml of methanol and the solution was then eluted through 1 g of Dowex® 50W-X8 (pyridinium form) ion exchange resin. The column was washed with 20 ml of 50% aqueous methanol and the solution was vacuum dried. The residue was suspended in a solution of 0.22 ml of tris-n-octylamine in 1.6 ml of methanol and, then, stirred for 30 minutes and finally dried under vacuum at 30° C. The resulting residue was suspended in 1 ml N,N-dimethylformamide and dried under vacuum at 30° C. This procedure was repeated three times. The resulting product was added to a solution of 2.24 ml of dioxane, 0.096 ml of diphenyl chlorophosphate and 0.137 ml of tris-butylamine and the mixture was stirred for 3 hours at 25° C. Then, it was dried in a rotary evaporator and 16 ml of diethyl ether were added to the residue under vigorous shaking. The mixture was kept on ice for 30 minutes and then centrifuged at 1000 rpm for 5 minutes. The diethyl ether was removed and the residue was dissolved in 0.96 ml of dioxane and dried under vacuum at room temperature and the product was used as such in the successive step c).

b) AZT-5'-monophosphate tri-n-octylammoniun salt 120 mg (0.35 mmoles) of AZT-5'-monophosphate sodium salt were dissolved into 2 ml of water and 2 ml of methanol and the solution was eluted through 1 g Dowex® 50W-X8 (pyridinium form) ion exchange resin with 20 ml of 50% aqueous methanol and dried in a rotary evaporator. Then, 0.49 ml of tri-n-octylamine and 3.5 ml of methanol were added to the residual product and the mixture was stirred for 30 minutes and finally dried under vacuum at 30° C. The residue was suspended again in 1.75 ml of N,N-dimethylformamide and dried under reduced pressure (5 mmHg) at 30° C. This procedure was repeated three times to yield a product which was used as such in the successive step c).

c) Reaction

The activated hypoxanthine-2',3'-dideoxy-D-riboside-5'-monophosphate of step a) was dissolved into 0.9 ml of anhydrous pyridine and the mixture was added to the AZT-5'-monophosphate tri-n-octylammonium salt of step b). Afterward, 0.16 ml of hexamethylphosphoramide were added to the mixture that was then dried in a rotary evaporator. After addition of 0.2 ml of anhydrous pyridine, the mixture was stirred for 24 hours at 25° C. The residue was suspended into 5 ml of water by adjusting the pH value to 8 with 1N NaOH and the solution was extracted three times with 5 ml of diethyl ether. The aqueous layer containing the product of the above title was separated and the product was purified according to the following step d).

d) Purification

Aliquots of 0.5 ml of the aqueous solution resulting from step c) were applied to a Sephadex® G10 column (55×1.3 cm) and eluted with water at a flow rate of 0.25 ml/ml. The fractions containing the title compound were further purified by using an HPLC apparatus equipped with a reverse phase column (C18 μBondapack®, 10 μm particle size). The solvent program was a linear gradient of methanol in water from 0 to 30% (v/v) at a flow rate of 1.5 ml/min in 30 minutes.

Under these conditions the compound of the above title shows a retention-time ($R_t$) of about 7 minutes.

The fractions showing a $R_t$ at the above value, were combined, loaded on 2 g of an ion exchange resin (Dowex® 50W-X8, H⁺ form) and eluted with 20 ml of water. The eluate was lyophilized giving the product of the above title with a 35% yield.

The MS-spectrum recorded with a Hewlett-Packard 5989A instrument shows a molecular ion at m/z 644 corresponding to the [M-1]− ion of the compound of the title.

The ultraviolet absorption spectrum in a phosphate buffer pH 4.9, 40% (v/v) methanol in water, exhibits an absorption maximum at 252 nm with a shoulder at 270 nm.

EXAMPLE 4

Preparation of di-(thymine-3'-azido-2',3'dideoxy-D-riboside)-5',5'-p1-P²-pyrophosphate a) Activation of AZT-5'-monophosphate 100 mg (0.26 mmoles) of AZT-5'-monophosphate sodium salt were dissolved in a mixture of 30 ml of water and 2 ml of methanol and the solution was eluted through 1 g of Dowex 50W-X8 (pyridinium form) ion exchange resin, with 20 ml of 50% aqueous methanol and then vacuum dried at room temperature. The residue was suspended in a mixture of 0.45 ml of tri-n-octylamine and 3.2 ml of methanol and stirred for 30 minutes at 25° C., then, it was dried under vacuum at room temperature. The residue was dissolved in 2 ml of N,N-dimethylformamide and dried under reduced pressure (5 mmHg). The procedure was repeated three times. Afterwards, 4.48 ml of dioxane, 0.2 ml of diphenyl chlorophosphate and 0.27 ml of tri-n-butylamine were added to the residue and, after stirring for 3 hours at 25° C., the mixture was dried at a reduced pressure (5 mmHg) at 30° C. Then, 16 ml of hexane were added to the residue under vigorous shaking and the mixture was kept on ice for 30 minutes before centrifugation at 1000 rpm for 5 minutes. The residue was dissolved in 2.0 ml of dioxane and dried under vacuum. The recovered product was used as such in the successive step c).

b) AZT-5'-monophosphate tri-n-octylammonium salt 100 mg (0.26 mmoles) of AZT-5'-monophosphate sodium salt were dissolved into a mixture of 3 ml of water and 2 ml of 50% aqueous methanol and the solution was loaded on a column containing 1 g of Dowex® 50W-X8 (pyridinium form) ion exchange resin and eluted with 20 ml of 50% aqueous methanol. The eluate was vacuum dried. Then, 0.45 ml of tri-n-octylamine and 3.2 ml of methanol were added to the residue and the mixture was stirred for 30 minutes at 25° C. and, finally, dried under vacuum at room temperature. The residue was suspended in 2 ml of N,N-dimethylformamide and dried under reduced pressure (5 mmHg). This procedure was repeated three times yielding a product which was used as such in the successive step c). C) Reaction:

The activated AZT-5'-monophosphate of step a), was dissolved in 1.8 ml of anhydrous pyridine and the solution was added to the AZT-5'-monophosphate tri-n-octylammonium salt of step b) together with 0.32 ml of hexamethylphosphotriamide. After drying under vacuum at room temperature, 0.4 ml of anhydrous pyridine were added to the residue and the mixture was stirred for 24 hours at 25° C. After drying under vacuum at room temperature, the residue was suspended in 6 ml of water and, after adjusting the pH value to 8 with 1N NaOH, the mixture was extracted three times with 6 ml of diethyl ether. The aqueous layer containing the product of the above title was separated by centrifugation and the product was recovered and purified according to the following step d).

d) Purification

The aqueous solution resulting from the previous step c), was purified using a reverse phase HPLC column. Aliquots of 1 ml of the aqueous solution were applied to a Bio-sil® C18 HL 90–10 column (Biorad) (250×10 mm, 10 μm particle size) and eluted with a linear step gradient of ethanol in water as described below:

| % (v/v) Ethanol | Time (minutes) |
|---|---|
| 3 | 0' |
| 3 | 7' |
| 5 | 10' |
| 15 | 15' |
| 100 | 16' |
| 100 | 25' |

The compound of the above title was eluted with a $R_t$ of 11 minutes.

The fractions showing a $R_t$ at the above value, were combined, loaded on 2 g of an ion exchange resin (Dowex® 50W-X8, H⁺ form) and eluted with 30 ml of a mixture methanol:water 50:50 (v/v). The eluate was lyophilized giving the product of the above title with a 35% yield.

The MS-spectrum recorded with a Hewlett-Packard 5989A instrument shows a molecular ion at m/z 675.9 corresponding to the [M-1]− ion of the compound of the above title.

The ultraviolet absorption spectrum in a phosphate buffer pH 4.9, 40% (v/v) methanol in water, exhibits an absorption maximum at 265 nm.

The ¹H-NMR spectrum recorded at 200 MHz in the temperature range from 20° C. to 30° C. on a Varian Gemini spectrometer in D₂O, shows the most significant chemical shifts at (δ ppm): 1.639 (—CH₃), 2.225 (—O—CH₂), 3.943 (broad 1'—CH and 2'—CH₂), 4.275 (3'—CH), 5.955 (4'—CH), 7.439 (aromatic proton 6—CH).

EXAMPLE 5

Preparation of 5-fluorouracil-2'-deoxy-D-riboside, thymine-3'-azido-2',3'-dideoxy-D-riboside-5',5'-P¹, P²-pyrophosphate a) Activation of AZT-5'-monophosphate 70 mg (0.182 mmoles) of AZT-5'-monophosphate sodium salt were activated by following the same procedure as described under Example 4, step a), and the product was used as such in the following step c).

b) 5-Fluorouracil-2'-deoxy-D-riboside-5'-monophosphate tri-n-octylammoniun salt 100 mg (0.27 mmoles) of 5-fluorouracil-2'-deoxy-D-riboside-5'-monophosphate sodium salt were transformed into the corresponding tri-n-octylammoniun salt by following the same procedure described under Example 4, step b), and the product was used as such in the following step c).

C) Reaction

The activated AZT-5'-monophosphate of step a) was dissolved in 1 ml of anhydrous pyridine and the solution was added to the 5-fluorouracil-2'-deoxy-D-riboside-5'-monophosphate sodium salt of step b) together with 0.2 ml of hexamethylphosphotriamide. After drying under vacuum, 0.2 ml of anhydrous pyridine were added to the residue and the mixture was stirred at room temperature for 24 hours. After evaporation of the solvent in a rotary evaporator at 30° C., the residue was suspended in 5.3 ml of water and, after adjusting the pH value to 8 by adding iN NaOH, the mixture was extracted three times with 5 ml of diethyl ether. The aqueous layer containing the product of the above title was separated and the product was recovered and purified according to the following step d).

d) Purification

The aqueous solution resulting from step c) was applied to a column containing 2 g of Dowex® 1-X8 (C1-form) ion exchange resin which was previously conditioned with 5 mM HCl. The flow rate was 0.4 ml/minute. The column was washed with 10 ml of 5 mM HCl, then, a linear gradient of LiCl from 0 to 600 mM in 5 mM HCl at a -flow rate of 0.5 ml/min, was applied.

Fractions containing the title product were collected and pooled and the value of the pH was adjusted to 6.5 by adding 1M LiCl. The solution was then concentrated to a volume of 4 ml in a rotary evaporator at 30° C. The concentrated solution was further purified by HPLC using a reverse phase HPLC column ($\mu$Bondapacks® C18, 250×10 mm, 10 $\mu$m particle size) by eluting with water at a flow rate of 4 ml/minute and injections of 500 $\mu$l. The recovered fractions were lyophilized yielding 25 mg of the product of the title as lithium salt. This product was converted with a practically quantitative yield into the free acid compound of the title by following the same procedure as described in the last part of step d) of Example 4.

The MS-spectrum recorded with a Hewlett-Packard 5989A instrument shows a molecular ion at m/z 653 corresponding to the [M-1]− ion of the compound of the title.

EXAMPLE 6

Preparation of di-(5-fluorouracil-2'-deoxy-D-riboside)-5',5'-$P^1$,$P^2$-pyrophosphate a) Activation of 5-fluorouracil-2'-deoxy-D-riboside-5'-monoahosphate 100 mg (0.27 mmoles) of 5-fluorouracil-2'-deoxy-D-riboside-5'-monophosphate sodium salt were activated by following the same procedure as described under Example 4, step a).

b) 5-fluorouracil-2'-deoxy-D-riboside-5'-monophosphate tri-n-octylammonium salt 100 mg (0.27 mmoles) of 5-fluorouracil-2'-deoxy-D-riboside-5'-monophosphate sodium salt were transformed into the corresponding tri-n-octylammonium salt by following the same procedure described under Example 4, step b), and the product was used as such in the following step c).

C) Reaction

The activated 5-fluorouracil-2'-deoxy-D-riboside-5'-monophosphate sodium salt of step a) was dissolved in 1 ml of anhydrates pyridine and the solution was added to the 5-fluorouracil-2'-deoxy-D-riboside-5'-monophosphate tri-n-octylammonium salt of step b) together with 0.2 ml of hexamethylphosphotriamide. After drying under vacuum, 0.2 ml of anhydrous pyridine were added to the residue and the mixture was stirred at room temperature for 24 hours. After evaporation of the solvent in a rotary evaporator at 30° C., the residue was suspended in 6 ml of water and, after adjusting the pH value to 8 by adding 1N NaOR, the mixture was extracted three times with 6 ml of diethyl ether. The aqueous layer containing the product of the above title was separated and the product was recovered and purified according to the following step d).

d) Purification

The aqueous solution resulting from step c) was applied to a column containing 2 g of Dowex® 1-X8 (C1-form) ion exchange resin which was previously conditioned with 5 mM Cl. The flow rate was 0.4 ml/min. The column was washed with 10 ml of 5 mM HCl, then a linear gradient of LiCl from 0 to 600 mM in 5 mM HCl at a flow rate of 0.4 ml/min, was applied.

Fractions containing the product of the above title were collected and pooled together and the pH was adjusted to 6.5 by the addition of 1M LiCl. The solution was then concentrated at a volume of 2 ml in a rotary evaporator at 30° C., then the compound was precipitated by adding a double volume of a mixture of ethanol:acetone 1:4 (v/v), in ice. The precipitated compound was finally washed with acetone and ether and dried with a gentle stream of nitrogen yielding the lithium salt of the compound of the above title which was converted to the free acid by following the same procedure described in the last part of step d) of Example 3.

Yield 30%.

The MS-spectrum recorded with a Hewlett-Packard 5989A instrument shows a molecular ion at m/z 633 corresponding to the [M-1]− ion of the compound of the title.

The ultraviolet absorption spectrum in a phosphate buffer pH 4.9, 40% (v/v) methanol in water, exhibits an absorption maximum at 269 nm.

We claim:

1. A dinucleoside-5',5'-$P^1,P^2$-pyrophosphate of the formula (I):

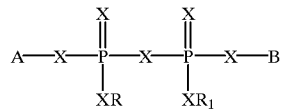

wherein:
the symbols A and B each independently represent a 5'-C' radical of a non-naturally occurring nucleoside selected from 1-thyminyl-3-azido-2,3-dideoxy-D-riboside and 1-uracilyl-3-azido-2,3-dideoxy-D-riboside;
the symbols X each independently represent oxygen or sulfur;
the symbols R and $R_1$ each independently represent hydrogen or an alkyl group of from 1 to 10 carbon atoms, which may optionally contain an unsaturation and/or one or two substituents selected from hydroxy, mercapto, chloro, iodo, fluoro, bromo, amino, $(C_1-C_4)$ alkylamino, di-$(C_1-C_4)$alkylamino, $(C_1-C_4)$alkoxy and $(C_1-C_4)$alkylthio;
and the addition salts of the compounds of formula (I) wherein R and/or $R_1$ represent hydrogen with bases providing biologically acceptable cations.

2. A dinucleoside of claim 1 wherein the symbol A represents a 5'-C' radical of a non-naturally occurring nucleoside selected from:
1-thyninyl-3-azido-2, 3-dideoxy-D-riboside and 1-uracilyl-3-azido-2,3-dideoxy-D-riboside;
the symbol B represents a 5'-C' radical of a non-naturally occurring nucleoside selected from:
1-thyminyl-3-azido-2,3-dideoxy-D-riboside and 1-uracilyl-3-azido-2,3-dideoxy-D-riboside;
one or two of the symbols X selected from those which are directly linked through a double bond to the phosphorous atom(s) and those that are part of the moiety XR and $XR_1$ represent(s) oxygen or sulfur and each of the other X represents oxygen;
the symbols R and $R_1$ each independently represent hydrogen or an alkyl radical of 1 to 4 carbon atoms;
and the addition salts of the compounds wherein R and/or $R_1$ represent hydrogen with bases providing biologically acceptable cations.

3. A compound as in claim 2 wherein all the symbols X represent oxygen, R and $R_1$ represent hydrogen, and their salts with biologically acceptable cations.

4. A compound of claim 2 wherein each of the symbols A and B represents a 5'-C' radical of a non-naturally occurring nucleoside in the following combinations:

1)
  A: 1-thyminyl-3-azido-2,3-dideoxy-D-riboside
  B: 1thyminyl-3-azido-2,3-dideoxy-D-riboside
2)
  A: 1-(5-fluoro)uracilyl-2-deoxy-D-riboside
  B: 1-thyminyl-3'-azido-2,3-dideoxy-D-riboside
3)
  A: 1-thyminyl-3-azido-2,3dideoxy-D-riboside
  B: 9-hypoxanthinyl-2,3-dideoxy-D-riboside
4)
  A: 1-thyminyl-3azido-2,3-dideoxy-D-riboside
  B: 1-cytosinyl-2,3-dideoxy-D-riboside
5)
  A: 1-thyminyl-3-azido-2,3-dideoxy-D-riboside
  B: 9-adeinyl-2,3-dideoxy-D-riboside
6)
  A: 1-uracilyl-3-azido-2,3-dideoxy-D-riboside
  B: 1-uracilyl-3-azido-2,3-dideoxy-D-riboside
7)
  A: 1-thyminyl-3-azido-2,3-dideoxy-D-riboside
  B: 1-uracilyl-3-azido-2,3-dideoxy-D-riboside
8)
  A: 1-uracilyl-3-azido-2,3-dideoxy-D-riboside
  B: 9-hypoxanthinyl-2,3-dideoxy-D-riboside
9)
  A: 1-thyninyl-3-azido-2,3-dideoxy-D-riboside
  B: 9-guaninyl-2,3-dideoxy-D-riboside and
10)
  A: 1-uracilyl-3-azido-2,3-dideoxy-D-riboside
  B: 9-guaninyl-2,3-dideoxy-D-riboside;
each of the symbols X represent oxygen;
each of the symbols R and $R_1$ represents hydrogen;
and their addition salts with bases providing biologically acceptable cations.

5. A compound of claim 4 wherein:
i)
  A represents a 5'-C' radical of a non-naturally occurring nucleoside which is 1-thyrinyl-3-azido-2,3-dideoxy-D-riboside, and
  B represents a 5'-C' radical of a non-naturally occurring nucleoside which is 9-hypoxanthinyl-2,3-dideoxy-D-riboside; or
ii)
  each of the symbols A and B represents a 5'-C' radical of a non-naturally occurring nucleoside which is 1-thyminyl-3-azido-2,3-dideoxy-D-riboside; or
iii)
  A represents a 5'-C' radical of a non-naturally occurring nucleoside which is 1-(5-fluoro)uracilyl-2-deoxy-D-riboside, and B represents a 5'-C' radical of a non-naturally occurring nucleoside which is 1-thyminyl-3-azido-2,3-dideoxy-D-riboside;
each of the symbols X represents oxygen;
each of the symbols R and R₁ represents hydrogens;
and their sodium and potassium salts.

6. A compound of claim 5 wherein:

each of the symbols A and B represents a 5'-C' radical of a non-naturally occurring nucleoside which is 1-thyminyl-3-azido-2,3-dideoxy-D-riboside;
each of the symbols X represents oxygen;
each of the symbols R and R₁ represents hydrogen;
and the sodium and potassium salts thereof.

7. A method of treating HIV in a patient in need thereof, comprising administering to said patient an effective anti-HIV amount of any of the compounds of claim 5, letter i), ii) and iii).

8. A method of treating HIV infections, in a patient in need thereof, comprising administering-to said patient an effective anti-HIV amount of a compound of any of claims 1 to 4 wherein at least one of the symbols A and B represents a 5'-C' radical of a non-naturally occurring nucleoside selected from: 1-thyminyl-3-azido-2,3-dideoxy-D-riboside, 1-uracilyl-3-azido-2,3-dideoxy-D-riboside, 9-guaninyl-2,3-dideoxy-D-riboside, 9-hyoxanthinyl-2,3-dideoxy-D-riboside, 1-cytosinyl-2,3-dideoxy-D-riboside and 9-adeninyl-2,3-dideoxy-D-riboside.

9. A method of treating HIV infections, in a patient in need thereof, comprising administering to said patient an effective anti-HIV amount of a compound of claim 6.

10. A pharmaceutical composition comprising a dinucleoside-5',5'-P¹,P²-pyrophosphate of the formula (I):

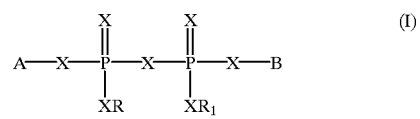

as defined in claims 1–6 wherein:
the symbols A and B, each independently represents a 5'-C' radical of a non-naturally occurring nucleoside selected from 1-thyminyl-3-azido-2,3dideoxy-D-riboside, 1-(5-fluoro)uracilyl-2-deoxy-D-riboside, 1-uracilyl-3-azido-2,3-dideoxy-D-riboside, 9-guaninyl-2,3-dideoxy-D-riboside, 9-hypoxanthinyl-2,3-dideoxy-D-riboside, 1-cytosinyl-2,3-dideoxy-D-riboside, and 9-adeninyl-2,3-dideoxy-D-riboside;
the symbols X each independently represent oxygen or sulfur;
the symbols R and R₁ each independently represent hydrogen or an alkyl group of from 1 to 10 carbon atoms;
and the addition salts of the compounds of formula (I) wherein R and/or R₁ represent hydrogen with bases providing biologically acceptable cations in combination with a pharmaceutically acceptable carrier.

11. A compound of claim 2 wherein the biologically acceptable cations are sodium cations.

12. A compound of claim 2 wherein the biologically acceptable cations are potassium cations.

13. A compound according to claim 3 wherein biologically acceptable cations are sodium cations.

14. A compound of claim 3 wherein the biologically acceptable cations are potassium cations.

15. A compound according to claim 4 wherein biologically acceptable cations are sodium cations.

16. A compound of claim 4 wherein the biologically acceptable cations are potassium cations.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION:  /desc = "Synthetic oligonucleotide"

(iv) ANTI-SENSE: NO (xi) SEQUENCE DESCRIPTION: SEQ ID NO: 1:

GGCATATCCT ATTCAAACAG                                                         20

(2) INFORMATION FOR SEQ ID NO: 2:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthetic oligonucleotide"

(iv) ANTI-SENSE: NO (xi) SEQUENCE DESCRIPTION: SEQ ID NO: 2:

CCTATATTTT ACGTTGAGAA                                                         20

(2) INFORMATION FOR SEQ ID NO: 3:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthetic oligonucleotide"

(iv) ANTI-SENSE: YES (xi) SEQUENCE DESCRIPTION: SEQ ID NO: 3:

TATGGTTTAC TGCCTTCTCT                                                         20

(2) INFORMATION FOR SEQ ID NO: 4:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthetic oligonucleotide"

(iv) ANTI-SENSE: YES (xi) SEQUENCE DESCRIPTION: SEQ ID NO: 4:

GAATTCGGTC TTTCATGGGA                                                         20

(2) INFORMATION FOR SEQ ID NO: 5:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthetic oligonucleotide"

(iv) ANTI-SENSE: NO (xi) SEQUENCE DESCRIPTION: SEQ ID NO: 5:

ACATGGAGTG GGGGGCCTTT GG                                                      22

(2) INFORMATION FOR SEQ ID NO: 6:

(i) SEQUENCE CHARACTERISTICS:

```
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(iv) ANTI-SENSE: YES (xi) SEQUENCE DESCRIPTION: SEQ ID NO: 6:

GTTGCGGACG ATTTCACCCA GG                                              22
```